US00PP30122P3

(12) United States Plant Patent
Byrne et al.

(10) Patent No.: US PP30,122 P3
(45) Date of Patent: Jan. 22, 2019

(54) NECTARINE TREE NAMED 'SMOOTH DELIGHT THREE'

(50) Latin Name: ***Prunus persica* var. *nucipersica***
Varietal Denomination: Smooth Delight Three

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/330,676

(22) Filed: Oct. 26, 2016

(65) Prior Publication Data

US 2018/0116082 P1 Apr. 26, 2018

(51) Int. Cl.
*A01H 5/08* (2018.01)
*A01H 6/74* (2018.01)

(52) U.S. Cl.
USPC ..... Plt./188
CPC ..... *A01H 6/7454* (2018.05); *A01H 5/08* (2013.01)

(58) Field of Classification Search
USPC ..... Plt./187, 188, 189
See application file for complete search history.

(56) References Cited

U.S. PATENT DOCUMENTS

| | | | |
|---|---|---|---|
| PP1,884 | P | 11/1958 | Swim |
| PP5,245 | P | 6/1984 | Zaiger |
| PP7,953 | P | 8/1992 | Bradford et al. |
| PP9,332 | P | 10/1995 | Zaiger et al. |
| PP9,871 | P | 4/1997 | Sherman |
| PP14,627 | P3 | 3/2004 | Byrne et al. |
| PP14,629 | P3 | 3/2004 | Byrne et al. |
| 2016/0205843 | P1 | 7/2016 | Bryne et al. |

OTHER PUBLICATIONS

UPOV-PLUTO :Plant Variety Database Dec. 15, 2017 citation for 'TX3B323LWN' retrieved on Dec. 18, 2017 (1 page).*
Brooks, R.M., Double Delight, Earligold, and June Gold peaches, 1969, Fruit Varieties J., 13:22.
Brooks et al., Register of New Fruit and Nut Varieties, 1997, 3rd Edition, American Society of Horticultural Science Press, Alexandria, VA.
Byrne et al., Zest peach series: Five medium chill yellow-fleshed cultivars, 2014, HortScience, 49(4):506-508.
Byrne et al., "TexRoyal" a medium chilling peach, 1991, HortScience, 26(10):1338-1340.
Byrne et al., "TexKing" an early ripening medium chill peach, 2004, HortScience, 39: 442-443.
Byrne et al., "TexPrince" a mid-season medium chill peach, 2004, HortScience, 39(3):631-632.
Ramming et al., "Mayfire" nectarine, 1987, Fruit Var. J., 41(2):80-81.
Sherman, et al., "Sunmist" nectarine, 1995, HortScience, 30(1): 155.
Sherman et al., "Flordaglo" A white flesh peach for central Florida, 1988, Fla. Agric. Exp. Stn. Circular, S-345.

* cited by examiner

*Primary Examiner* — Susan McCormick Ewoldt
(74) *Attorney, Agent, or Firm* — Ramey & Schwaller, LLP

(57) ABSTRACT

Disclosed is a new variety of *Prunus persica* named 'SMOOTH DELIGHT THREE'. This new variety, which requires approximately 500 chilling units of dormancy, is considered to be a nectarine tree of early season maturity, which ripens in late May to early June in the medium chill zone of Texas and produces white fleshed fruit that are very firm, attractively colored, and suitable for both local and long-distance shipping.

5 Drawing Sheets

Latin name: *Prunus persica* var. *nucipersica*.
Variety: Smooth Delight Three.

BACKGROUND OF THE INVENTION

Field of the Invention

This invention relates to nectarine trees referred to as a variety of *Prunus persica* var. *nucipersica* named 'Smooth Delight Three'. 'Smooth Delight Three', which requires approximately 500 chilling units of dormancy, produces an exceptionally high quality, firm, subacid, clingstone nectarine that matures early in the season.

SUMMARY OF THE INVENTION

The 'Smooth Delight Three' nectarine to provides very firm, well sized, early ripening, attractive, subacid, high quality, white-fleshed nectarine for the fresh market. The new nectarine will ripen in late May to early June in the medium chill zone of Texas and similar regions.

Origin of the Variety

The present nectarine tree was the result of controlled crosses made each year to produce seedling populations from which improved progenies are selected.

The 'Smooth Delight Three' (TX3B323LWN) nectarine [*Prunus persica* var. *nucipersica* (Batsch) L.] was selected from the high density seedling selection in 2006 from a population derived from selfing the selection TX4C188LWN (unreleased, not patented). TX4C188LWN originated from a cross between female parent 'Sunmist' (U.S. Plant Pat. No. 9,871) a white-fleshed, acid-flavored nectarine released by Florida, and the male parent 'Arctic Star' (U.S. Plant Pat. No. 9,332) a white-fleshed nectarine with a subacid flavor. 'Sunmist' is derived from a cross between 'Flordaglo' (not patented, Sherman and Lyrene, 1988) and 'Mayfire' (not patented, Ramming and Tanner, 1987) whereas 'Arctic Star' is a hybrid between an unknown white nectarine and 'Mayglo' nectarine (U.S. Plant Pat. No. 5,245). Resulting seed from this 'Sunmist' x 'Arctic Star' cross were planted in 2000 in a high density breeding orchard in College Station, Tex. In 2003, the selection TX4C188LWN was marked for subsequent observation and noted as having exceptional characteristics. In 2004, selfed seed was collected and embryo rescued. The resulting seedlings were planted in the high density seedling selection field in 2005. In 2006, TX3B323LWN was selected for its attractiveness, low acidity, high soluble solids, and productivity.

'Smooth Delight Three' differs from its parent TX4C188LWN as it has a higher blush, rounder tip and a slightly higher Brix content as grown in the medium chill zone of Texas. 'Smooth Delight Three' differs from its grandmother 'Sunmist' as it has a subacid flavor whereas 'Sunmist' has a higher acid content. Although both 'Smooth Delight Three' and 'Arctic Star' have white, subacid flesh, 'Smooth Delight Three' blooms a week before and has a rounder shape than 'Arctic Star' as grown in the medium chill zone of Texas.

Two-year and older trees of the variety were subsequently evaluated during the 2009 through 2013 fruit growing seasons in California (Clovis) and from 2009 to 2015 fruit growing seasons in the medium chill zone of Texas (Fairfield and College Station).

Asexual Reproduction of the Variety

'Smooth Delight Three' was bud grafted onto virus-free Nemaguard (not patented, Brooks and Olmo, 1997) peach rootstock in June 2006 at the nursery site in Oakdale, Calif. The variety was subsequently planted at the experimental orchard in the central portion of the San Joaquin Valley, near Fowler, Fresno County, Calif. and in two sites in Texas (College Station and Fairfield). Fruit from the resulting propagation has been evaluated during the period from 2009 to 2015 fruit seasons. This evaluation clearly demonstrated that the re-propagated trees were true to the characteristics of the original seedling in all observable aspects.

BRIEF DESCRIPTION OF THE DRAWINGS

This new variety of nectarine tree is illustrated by the accompanying photographic drawings and depicts the plant by the best possible color representation using color photography, wherein.

BOTANICAL DESCRIPTION OF THE VARIETY

Figure 1:
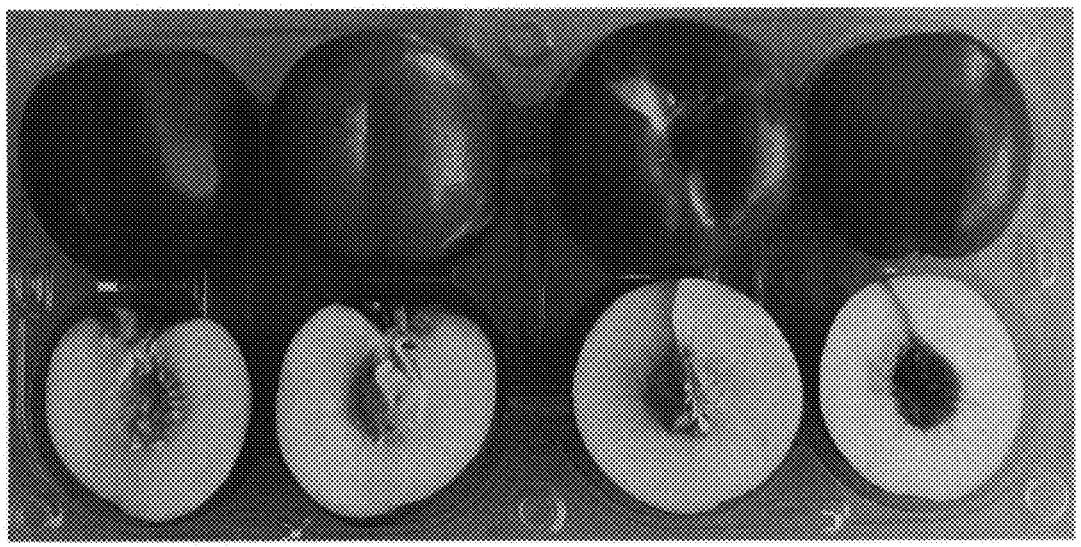
FIG. 1. 'Smooth Delight Three' fruit sample from the research plots in Clovis, Calif.
Figure 2:
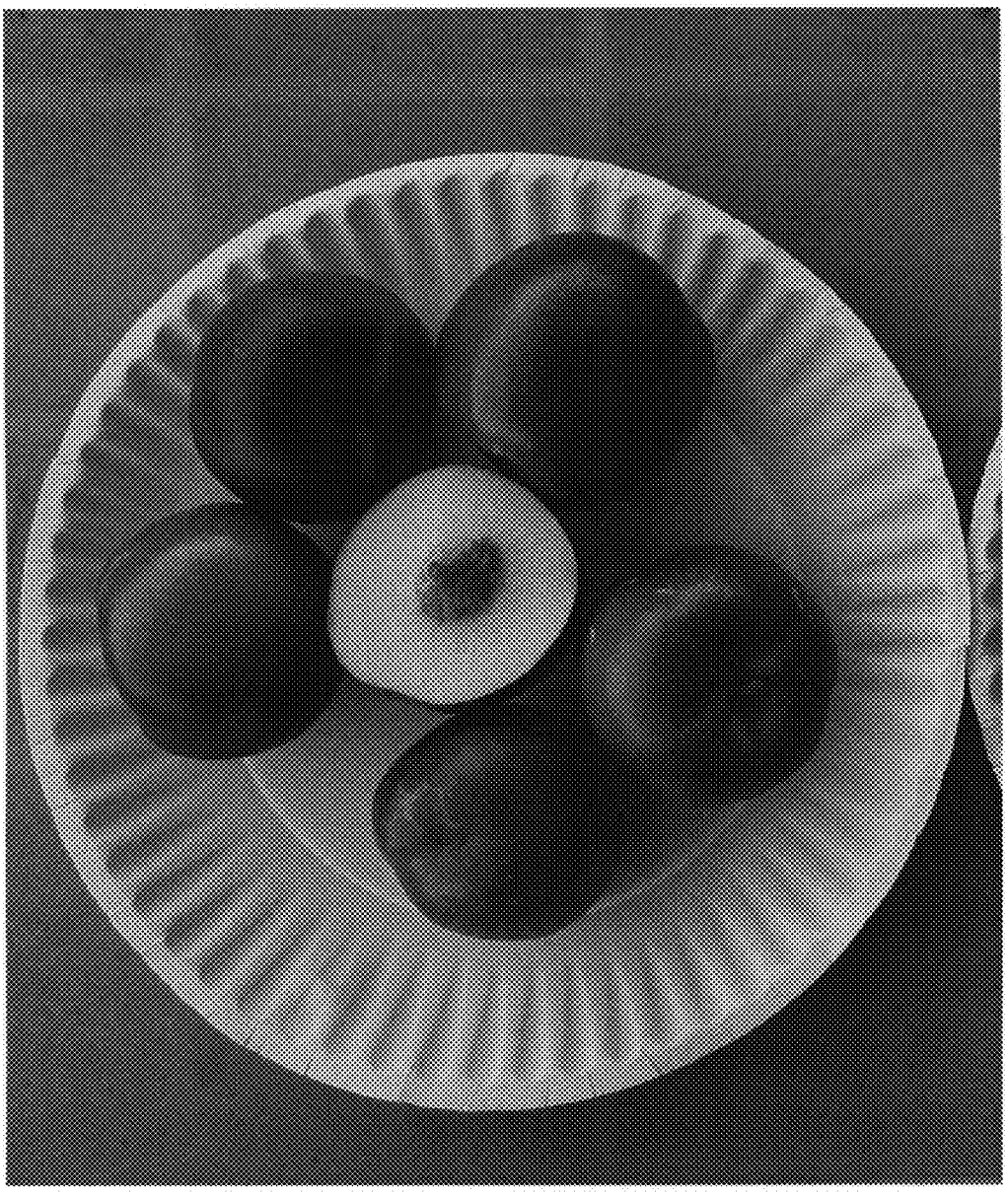
FIG. 2. Sample of 'Smooth Delight Three' showing the internal and external coloration of the fruit.
Figure 3:
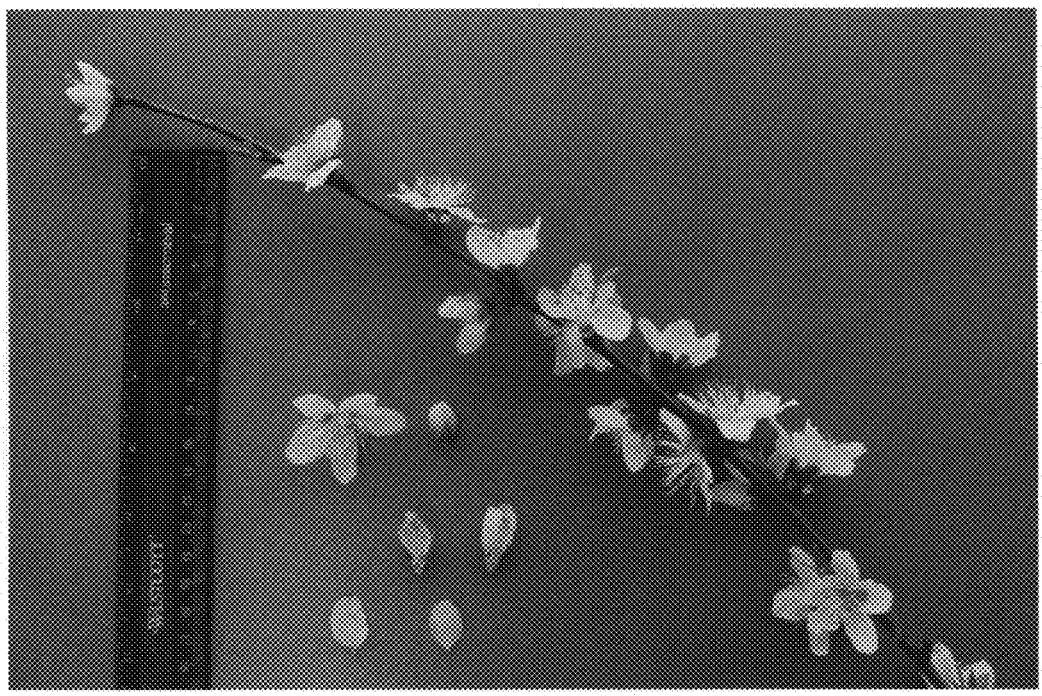
FIG. 3. The showy flowers of the 'Smooth Delight Three' nectarine from the experimental plot in Fairfield, Tex. The ruler is demarcated in millimeters.
Figure 4:
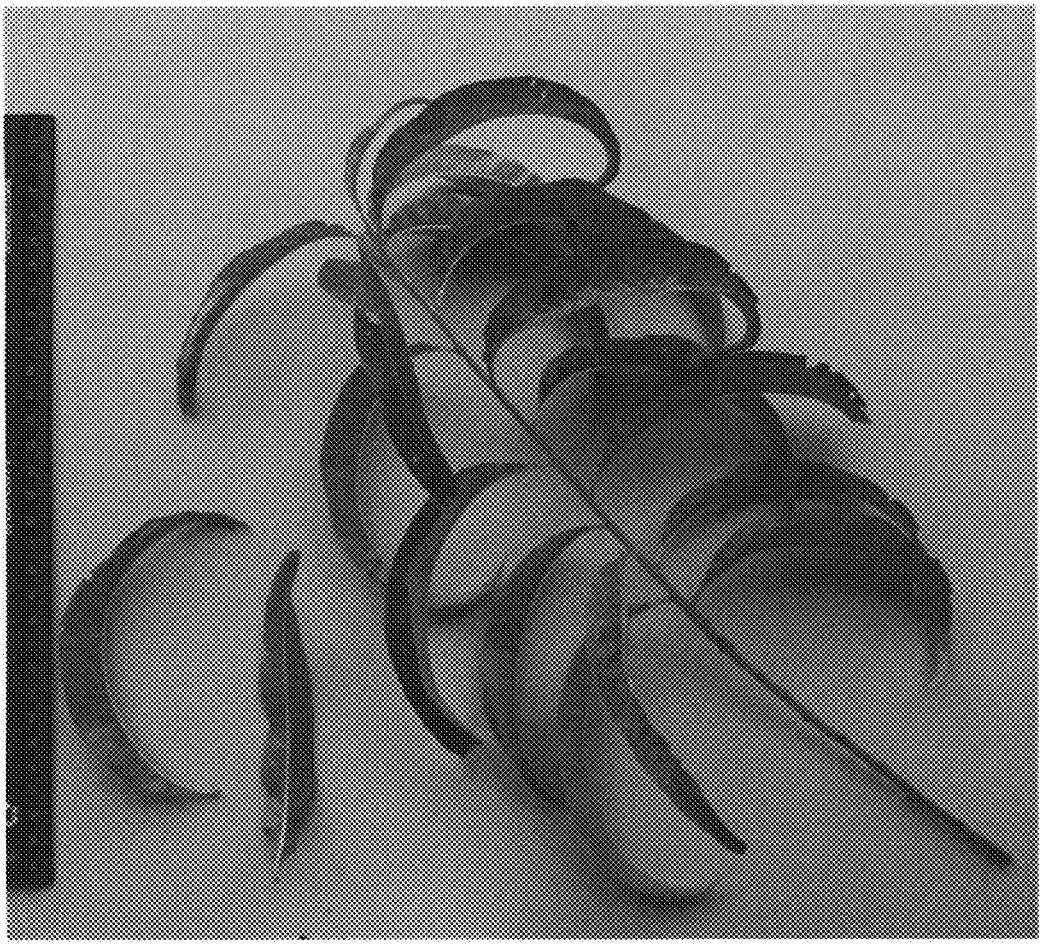
FIG. 4. Color photograph of a one-year old shoot and leaves showing both adaxial and abaxial surfaces from a three-year-old tree grown in College Station, Tex. The ruler is demarcated in millimeters.
Figure 5:
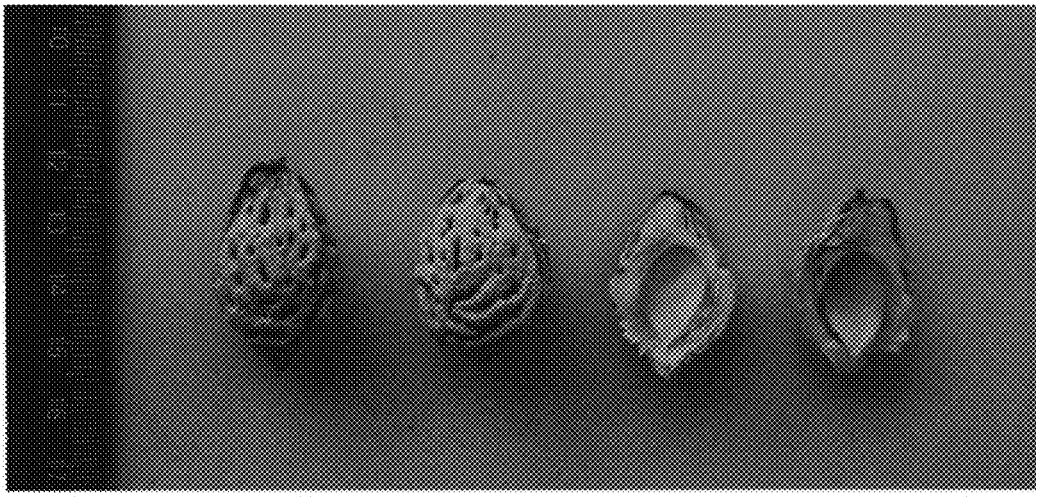
FIG. 5. Color photograph showing the pits (endocarp) of 'Smooth Delight Three' from a four-year old tree. The ruler is demarcated in millimeters.

Referring more specifically to the pomological details of this new and distinct variety of nectarine tree, the following has been observed under the ecological conditions prevailing at the experimental orchards in medium chill zone of Texas in College Station and Fairfield, Tex. All major color code designations are by reference to The R.H.S. Colour Chart (2001) provided by The Royal Horticultural Society of Great Britain. Colors are approximate as color depends on horticultural practices such as light level and fertilization rate, among others.

Tree:

*Size*.—Generally average to above average as compared to other common nectarine cultivars ripening in the early season of maturity. Observations done on a three-year old tree.

*Height*.—10-15 feet (3-4.5 m) at the end of the 2016 growing season on a three-year old tree.

*Width*.—5.5-6 feet (1.6-1.8 m) at the end of the 2016 growing season on a three-year old tree.

*Vigor*.—High.

*Density*.—Medium to high.

*Productivity*.—Productive.

*Shape*.—The trees are vigorous with the typical semi-spreading growth habit similar to 'TexKing' (U.S. Plant Pat. No. 14,627), 'TexPrince' (U.S. Plant Pat. No. 14,629), and 'TexRoyal' (not patented, Byrne and Bacon, 1991).

*Current season growth*.—The current season growth for the new variety was approximately 3.75 to 4.6 feet (1.1-1.4 m).

*Regularity of bearing*.—Regular, and considered hardy under typical environmental conditions of the medium chill region of Texas and the central San Joaquin Valley, Calif. conditions.

Trunk:

*Size*.—Approximately 2.75 inches (7 cm) in diameter when measured at a distance of approximately 12 inches (30.5 cm) above the soil level, at the end of the 2016 growing season on a three-year old tree.

*Bark texture*.—Considered moderately rough with numerous folds of papery scarf-like skin being present.

*Bark coloration*.—Dark brown with grey, R.H.S. colors present are N115A of the White Group, 166A-B and 175A-C of the Greyed-Orange Group, N200C-D of the Brown Group, 201D of the Grey Group and 202D of the Black Group.

Branches:

*Size*.—Considered medium for the variety.

*Thickness*.—Average (approximately 1.8-3.8 cm in diameter as measured 10 cm from the trunk on a three-year old tree) as compared to other varieties.

*Length*.—The length of the branches are limited by pruning to a 3 to 5 foot (~0.9-1.5 m) length depending on the position on the tree.

*Surface texture*.—Average and appearing furrowed on wood that is several years old.

*Lenticels*.—Numerous flat, oval lenticels present. The lenticels range in size from approximately 2 to 6 mm in width and were approximately 1-2 mm in height.

*Current season shoots*.—Surface texture — Substantially glabrous.

*Internode length*.—Approximately 2.5 to 3.8 cm as measured in the middle of a current season stem.

*Color of mature branches*.—The predominant colors are medium brown, 166B-C and 175C of the Greyed-Orange Group and 200D of the Brown Group.

*Current season shoots*.—Color — Light to medium brown (164A and 165B of the Greyed-Orange Group and 199A and N199C-D of the Grey-Brown Group). The color of new shoot tips is considered medium green (mainly 143C of the Green Group and 144B-C and N144D of the Yellow-Green Group) with a red blush present on the tips (180A of the Greyed-Red Group and 184B-C and 185B of the Greyed-Purple Group).

Leaves:

*Size*.—Considered slightly smaller than average for the species. Leaf measurements have been taken from vigorous upright current season growth approximately at mid-shoot on three-year old trees.

*Leaf length*.—Approximately 157 to 179 mm.

*Leaf width*.—Approximately 30 to 35 mm.

*Leaf thickness*.—Less than 1 mm.

*Leaf form*.—Lanceolate.

*Leaf tip form*.—Acuminate.

*Leaf upper surface color*.—Green varying among 137C and 138A of the Green Group and 144A of the Yellow-Green Group.

*Leaf lower surface color*.—Green varying among 145C and 154D of the Yellow-Green Group.

*Leaf mid-vein color*.—Light yellow green 145C and 154D of the Yellow-Green Group.

*Leaf margins*.—

*Form*.—Considered crenate.

*Uniformity*.—Considered generally uniform.

*Leaf petioles*.—

*Size*.—Considered medium long.

*Length*.—Approximately 9 to 12 mm.

*Thickness*.—Approximately 2 mm.

*Color*.—Light green to pale green N144D and 146C-D of the Yellow-Green Group.

*Leaf glands*.—

*Size*.—Approximately 1 to 1.5 mm in height and 0.5 to 1 mm in width.

*Number*.—Generally 3 to 4 per leaf located at the base of the leaf blade.

*Type*.—Reniform.

*Color*.—Green with brown N144D and 146C-D of the Yellow-Green Group and N199B-D of the Grey-Brown Group.

*Leaf stipules*.—

*Size*.—Average for the species.

*Length*.—Approximately 9 to 13 mm.

*Width*.—Less than 1 mm.

*Form*.—Lanceolate.

*Color*.—Light green N144A and 151A of the Yellow-Green Group with reddish brown tips 172A-B, 173A and 175A-B of the Greyed-Orange Group when young. The stipules are considered to be early deciduous.

*Ratio of wood (leaf) buds to flowering buds*.—1 to 2 flower buds per vegetative bud.

Flowers:

*Floral buds*.—

*General*.—The floral buds are considered to be medium to medium large in size, conic in form, and slightly appressed relative to the bearing shoot.

*Color*.—The bud scales are brown, (approximately 187A-B of the Greyed-Purple Group and 200A-C and N200A of the Brown Group). The buds are considered hardy under the typical climatic conditions found in the medium chill zone of Texas and the central San Joaquin Valley, Calif.

*Length*.—Approximately 5 mm on flower buds in late summer on current season wood.

*Width*.—Approximately 2 mm on flower buds in late summer on current season wood.

*Blooming type*.—Considered early in relation to other peach and nectarine cultivars commonly growing in the medium chill zone of Texas and the central San Joaquin Valley. Date of full bloom was between February 18th and February 27th during the period between 2009 and 2015. In the medium chill zone (College Station and Fairfield, Tex.), this nectarine bloomed with the peach 'Royal Zest Two' (U.S. Plant Pat. No. 28,172) (Byrne and Anderson, 2014) and 6-10 days before 'June Gold' (U.S. Plant Pat. No. 1,884 (Brooks, 1958). The estimated chilling requirement is between 500-550 CU.

*Flower fertility*.—Self-fertile.

*Flower type*.—Showy.

*Flower size*.—Flower diameter at full bloom is approximately 32 to 44 mm.

*Bloom quantity*.—Considered abundant.

*Flower bud frequency*.—Normally 1 to 2 per node.

*Petal size*.—

*General*.—Considered medium large for the species.

*Width*.—Approximately 12 to 14 mm.

*Length*.—Approximately 20 to 22 mm.

*Petal form*.—Broadly ovate.

*Petal count*.—Nearly always 5.

*Petal color*.—Light pink when young (Red-Purple Group 69B-C; Purple Group 75D), becoming slightly darker near the petal claw.

*Petal claw*.—

*Form*.—The claw is considered truncate in shape and has a medium size when compared to other varieties.

*Length*.—Approximately 1 to 1.5 mm.

*Width*.—Approximately 1 mm.

*Petal margins*.—Generally considered variable, from nearly smooth to slightly undulate.

*Petal apex*.—Generally — The petal apices appear slightly domed.

*Flower pedicel*.—

*Length*.—Considered medium to short, and having an average length of approximately 2 to 4 mm.

*Thickness*.—Considered average, approximately 1 mm.

*Color*.—A light green (Yellow-Green Group 144D and N144B-D).

*Floral nectaries*.—

*Color*.—Variable, from white to light yellow (Yellow Group 2D, 3D, 4C-D and 5D; White Group 155A-D).

*Hypanthium*.—

*Surface texture*.—Generally glabrous.

*Color*.—A brownish red to maroon with green (Red Group 46A and 53A; Yellow-Green Group 144A-B and 145A; Greyed-Orange Group 176A; Greyed-Red Group 178A-B; Greyed-Red Group 181A; Greyed-Purple Group 183A-C, 185A and 187C).

*Sepals*.—

*Surface texture*.—The surface has a short, fine, wooly texture.

*Size*.—Slightly smaller than average, and ovate in form.

*Length*.—4.8 to 5.7 mm on recently opened flowers.

*Width*.—3.9 to 5.2 mm on recently opened flowers.

*Color*.—A brownish red to maroon with green and grey (Red Group 46A and 53A; Yellow-Green Group 144A-B and 145A; Greyed-White Group 156A-D; Greyed-Orange Group 176A; Greyed-Red Group 178A-B; Greyed-Red Group 181A; Greyed-Purple Group 183A-C, 185A and 187C).

*Anthers*.—

*General*.—Average in size for the species. The anthers are about 1 mm in length and 0.5 mm in width.

*Color*.—Young anthers are reddish-orange with white and yellow (White Group 155A-D; Yellow-White Group 158A-D; Greyed-Orange Group N163A, 168A, 169A-B, 170A, 171B and N172A-B).

*Pollen production*.—Pollen is abundant, and is a yellow color (approximately Yellow Groups 5A-B and 12A-13B).

*Filaments*.—

*Size*.—Variable in length, approximately 13 to 15 mm, with the filaments equal to or slightly longer than the pistil.

*Color*.—White when young (approximately White Group 155A-D and N155C-D) and darkening to medium pink (Red-Purple Group 63B-C and 64D) with advanced maturity.

*Pistil*.—

*General*.—Average in size, but equal to or slightly shorter to the general anther height, overall.

*Length*.—Approximately 15 to 16 mm, including the ovary.

*Color*.—Considered a very light yellow-green when young (Yellow Group 1C-D and Yellow-Green Group 151A), and developing a medium-dark pink coloration (Red-Purple Group N57D, 62B-C and 63C) with advancing senescence.

*Surface texture*.—None present.

Fruit:

*Maturity when described*.—This early ripening, clingstone, subacid, melting flesh, white nectarine cultivar ripens about 85 days after full bloom. In the medium chill zone it ripens in late May to early June a few days before 'Royal Zest Two' depending on the year and site grown.

*Fruit quality*.—This nectarine has low acidity, good size, excellent quality and excellent attractiveness for an early ripening nectarine when properly managed and thinned. It has a mean soluble solid content similar to or higher than 'Royal Zest Two' when picked mature.

*Size*.—General — Medium large to large for the season and considered uniform.

*Average cheek diameter*.—Approximately 59 to 65 mm.

*Average suture diameter*.—Approximately 57 to 63 mm.

*Average axial diameter*.—Approximately 61 to 69 mm.

*Fruit form*.—Generally considered truncate with unequal halves. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex. No apparent callusing or stitching exists along the suture line.

*Color*.—59A-B and 60A-B of the Red-Purple Group.

*Ventral surface*.—Form — Considered uniform.

*Stem cavity*.—

*Size*.—Considered moderately shallow for the species.

*Width*.—Approximately 12 mm.

*Length*.—Approximately 14 to 18 mm.

*Depth*.—Approximately 7 to 12 mm.

*Fruit base*.—Flat.

*Fruit apex*.—Flat and depressed.

*Fruit stem*.—

*Length*.—Approximately 8 mm.

*Thickness*.—Approximately 3 mm.

*Color*.—Varies from 138A-B of the Green Group to 144A-C of the Yellow-Green Group.

*Fruit skin*.—Generally considered medium or average in thickness.

*Surface texture*.—Smooth, not pubescent. The glabrous skin has a medium glossiness.

*Skin acidity*.—Considered neutral.

*Tenacious to flesh*.—Yes at commercial maturity.

*Tendency to crack*.—Not observed.

*Skin color*.—Generally — Variable, with a high (~80-90%) percentage of the fruit surface covered with a blush as described below under Blush Color.

*Pubescence*.—Absent.

*Blush color*.—46A and 53A-B of the Red Group; 59A-B and 60A of the Red-Purple Group N77A of the Purple Group and 185A and 187A-B of the Greyed-Purple Group.

*Skin ground color*.—2D, 4D, 5D, 8D, 9D, 10D, 11D and 12D of the Yellow Group and 155A of the White Group.

*Flesh color*.—White, similar to 155A-D of the White Group with pink, 63A and 64B of the Red-Purple Group and 186A-B of the Greyed-Purple Group.

*Flesh fibers*.—Present, numerous and lightly colored. These fibers are present throughout the flesh.

*Stone cavity color*.—White, similar to 155A-D of the White Group with pink, 63A and 64B of the Red-Purple Group and 186A-B of the Greyed-Purple Group.

*Flesh texture*.—Generally, the flesh is considered firm and fine at commercial maturity.

*Ripening*.—Generally the fruit of the present variety ripens evenly.

*Flavor*.—Considered very sweet and a rich, with a subacid flavor.

*Soluble solids*.—Varies from 10 to 15 Brix depending on the site, weather and cultural care.

*Acidity*.—Varies from 2.1 to 4.5 meq/mL.

*Aroma*.—Pleasant and reasonably abundant.

*Eating*.—Generally considered very good to excellent, particularly for an early ripening variety.

Stone:

*Attachment*.—Clingstone (highly adherent) at commercial maturity.

*Stone size*.—Generally considered medium to medium-large relative to the ratio of stone to fruit size.

*Length*.—Approximately 33 to 35 mm.

*Width*.—Approximately 21 to 23 mm.

*Thickness*.—Approximately 16 to 17 mm.

*Fibers*.—Generally a few medium length fibers are attached along the entire surface of the stone.

*Stone form*.—Obovate.

*Stone base*.—The stone is medium.

*Base angle*.—The base angle of the stone is variable, but most frequently is considered slightly oblique to the stone axis.

*Hilum*.—Generally considered medium in size, and rather poorly defined as is common in very early ripening varieties. The hilum is approximately 6 to 7 mm long and less than 1 mm wide.

*Form*.—Considered oval.

*Apex shape*.—Medium to wide.

*Stone shape*.—Considered variable. The stone normally ovoid to elongated.

*Stone surface*.—

*Surface texture*.—Single Pits with rosettes of pits.

*Ridges*.—Numerous fine ridges are present basally, and converge towards the base of the stone.

*Ventral edge*.—None to small.

*Dorsal edge*.—Shape — Grooved and having moderately rough edges.

*Stone color*.—The color of the dry stone is light brown 165C-D of the Greyed-Orange Group. The color of the inside surface of the endocarp is primarily 164D and 165D of the Greyed-Orange Group.

*Tendency to split*.—Splitting is relatively uncommon.

*Kernel*.—The kernel fills the endocarp at harvest and measures approximately 2 to 4 mm in thickness, 10 to 16 mm in width, and 15 to 19 mm in length. When dried, the kernel measures approximately 1 to 3 mm in thickness, 9 mm in width, and 14 to 15 mm in length. The colors of the dried kernels are primarily 158A of the Yellow-White Group and 164A, 165B-C and 166D of the Greyed-Orange Group. The seed is not viable if stratified and germinated without using an embryo rescue technique.

*Use*.—The subject fresh market variety, 'Smooth Delight Three', is considered to be an early season maturity, which produces low-acid, white fleshed fruit that are very firm, attractively colored, and suitable for both local and long-distance shipping.

*Keeping quality*.—Good to very good.

*Resistance to insects and disease*.—No particular susceptibilities were noted or claimed. No observations have been made on resistance for either peach rust (Tranzschelia discolor) or bacterial leaf spot (Xanthomonas campestris pv. pruni (E. F. Smith) Dye).

*Shipping quality*.—Above average.

Although the new variety of nectarine tree possesses the described characteristics when grown under the ecological conditions prevailing in the medium chill zone of Texas it will be understood that variations of the usual magnitude and characteristics incident to the changes in growing conditions, fertilization, pruning, and pest control are to be expected.

REFERENCES

Anon. 2001. R.H.S. Colour Chart. The Royal Hort. Soc., London.

Brooks, R. M. 1958. Double Delight, Earligold, and June Gold peaches. Fruit Var. J. 3:22. U.S. Plant Pat. No. 1,884.

Brooks, R. M. and H. P. Olmo. 1997. Register of New Fruit and Nut Varieties. 3rd Edition. American Society of Horticultural Science Press, Alexandria, Va.

Byrne, D. H. and N. Anderson. 2014. Zest peach series: Five medium chill yellow-fleshed cultivars. HortScience 49(4):506-508.

Byrne, D. H and N. Anderson. 2015. Peach tree, Royal Zest Two. U.S. Plant Pat. No. 28,172, Jul. 11, 2017.

Byrne, D. H. and T. A. Bacon. 1991. 'TexRoyal', a medium chilling peach. HortScience 26(10):1338-1340.

Byrne, D. H. and T. A. Bacon. 2004a. TexKing, an early ripening medium chill peach. HortScience 39: 442-443.

Byrne, D. H. and T. A. Bacon. 2004b. TexPrince, a mid-season medium chill peach. HortScience 39(3):631-632.

Ramming, D. W. and O. Tanner. 1987. 'Mayfire' nectarine. Fruit Var. J. 41(2):80-81.

Sherman, W. B. 1997. Nectarine tree called 'Sunmist'. U.S. Plant Pat. No. 9,871. 29 Apr. 1997.

Sherman, W. B., P. C. Andersen, and P. M. Lyrene. 1995. 'Sunmist' nectarine. HortScience 30(1): 155.

Sherman, W. B. and P. M. Lyrene. 1988. Flordaglo, A white flesh peach for central Florida. Fla. Agric. Exp. Stn. Circular S-345.

Zaiger, C. F. 1982. Nectarine tree — May Glo. U.S. Plant Pat. No. 5,245. Jun. 12, 1984.

Zaiger, C. F., G. N. Zaiger, L. M. Gardner, and G. G. Zaiger. 1995. Nectarine tree 'Arctic Star'. U.S. Plant Pat. No. 9,332. 17 Oct. 1995.

We claim:

1. A new and distinct *Prunus persica* tree, substantially as illustrated and described herein.

* * * * *